United States Patent [19]

Young

[11] Patent Number: 4,526,791
[45] Date of Patent: * Jul. 2, 1985

[54] BIOCONVERSION OF AGRICULTURAL WASTES INTO PROTEINACEOUS ANIMAL FEED

[75] Inventor: Murray M. Young, Waterloo, Canada

[73] Assignee: University of Waterloo, Waterloo, Canada

[*] Notice: The portion of the term of this patent subsequent to Apr. 12, 2001 has been disclaimed.

[21] Appl. No.: 452,515

[22] Filed: Dec. 23, 1982

Related U.S. Application Data

[63] Continuation-in-part of Ser. No. 115,508, Jan. 25, 1980, abandoned.

[30] Foreign Application Priority Data

Jan. 30, 1979 [GB] United Kingdom ............... 7903151

[51] Int. Cl.³ ............................................. C12N 1/24
[52] U.S. Cl. ...................................... 426/53; 426/56; 426/636; 426/807; 435/251; 435/252; 435/911
[58] Field of Search ............... 435/68, 251, 252, 911; 426/2, 53, 56, 59, 623, 630, 635, 636, 807

[56] References Cited

U.S. PATENT DOCUMENTS

| | | | |
|---|---|---|---|
| 3,627,095 | 12/1971 | Srinivasan | 426/656 X |
| 3,838,198 | 9/1974 | Bellamy et al. | 426/56 X |
| 3,846,558 | 11/1974 | Stevens | 426/56 X |
| 3,904,768 | 9/1975 | Hruby | 426/53 |
| 3,937,845 | 2/1976 | Han et al. | 426/807 X |
| 3,973,043 | 8/1976 | Lynn | 426/56 X |
| 4,115,593 | 9/1978 | Henry | 426/56 X |

OTHER PUBLICATIONS

Young et al., "Single Cell Protein from Various Chemically Pretreated Wood Substrates Using Chaetomium Cellulolyticum", Chem. Abst. 1978 87624v.

Young et al., "SCP Production by Chaetomium Cellulolyticum a New Thermotolerant Cellulolytic Fungus", Chem. Abst. 1977 153935j.

Primary Examiner—R. B. Penland
Attorney, Agent, or Firm—Sim & McBurney

[57] ABSTRACT

Agricultural waste material, including animal manure and crop wastes, are converted into proteinaceous animal feed products by a fermentation process using the fungus, *Chaetomium cellulolyticum*.

12 Claims, 1 Drawing Figure

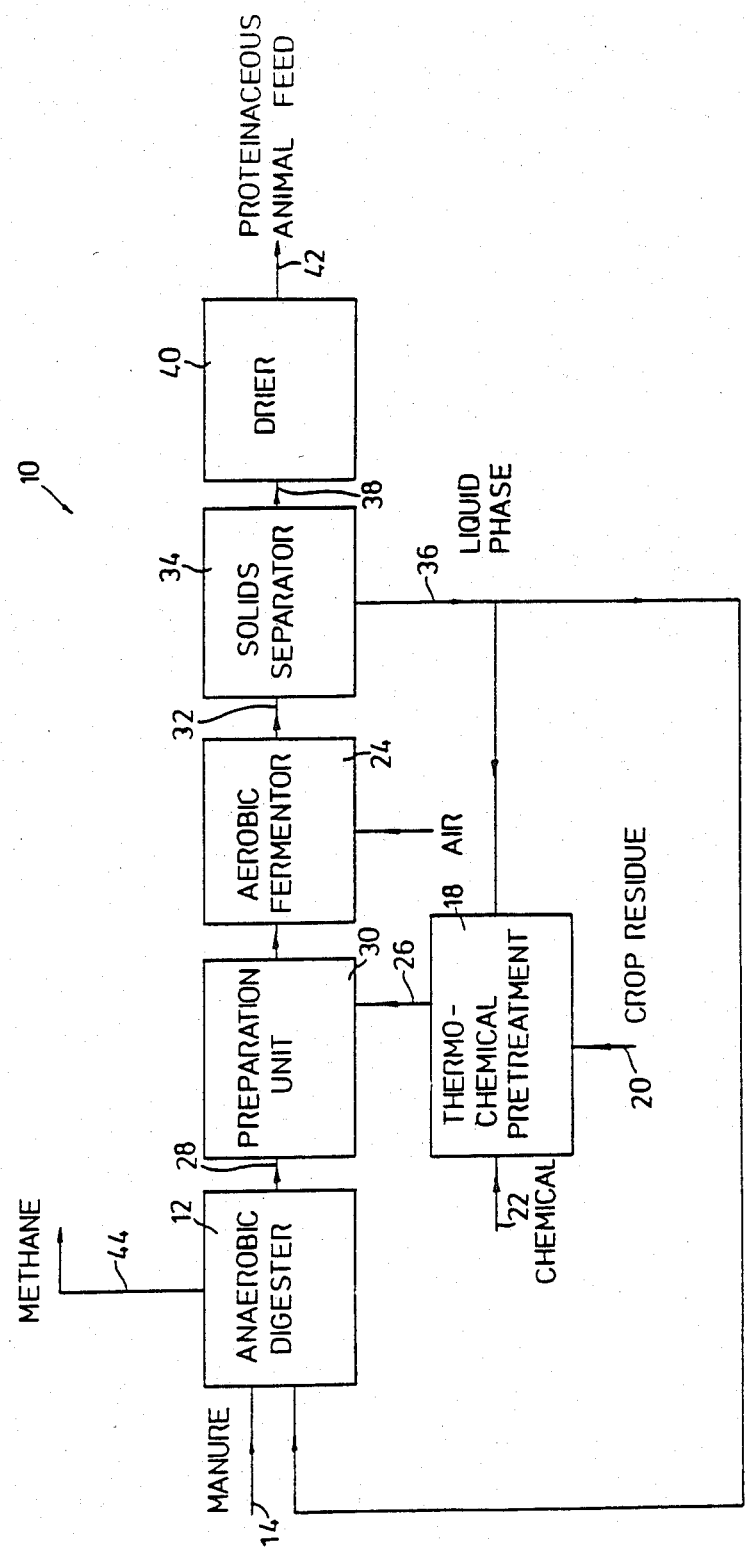

BIOCONVERSION OF AGRICULTURAL WASTES INTO PROTEINACEOUS ANIMAL FEED

REFERENCE TO RELATED APPLICATION

This application is a continuation-in-part of application Ser. No. 115,508 filed Jan. 25, 1980 now abandoned.

FIELD OF INVENTION

The present invention relates to the bioconversion of agricultural waste materials to form proteinaceous animal feed products or supplements. In the following description, concentrations of substances are expressed as W/V (for weight per unit volume of total mixture), as W/W (for weight per unit weight of total mixture) or as DM (for weight per unit weight of total mixture on a dry matter basis).

BACKGROUND TO THE INVENTION

Vast quantities of cellulosic materials occur universally as surplus and waste residues of agricultural operations. In particular, they occur in the form of cellulosic crop residues, usually the straws of cereal grains, for example, wheat, barley, corn, rice, oats and rye (sometimes called stovers, for example, cornstover) and sugarcane bagasse, and in the form of animal manure, such as, cattle, swine and poultry manure.

There have been prior suggestions to convert components of these waste materials to useful proteinaceous materials by fermentation, but generally speaking such prior procedures have been uneconomic and/or do not utilize all the components of the waste material.

SUMMARY OF INVENTION

In accordance with the present invention, there is provided an improved process for the formation of proteinaceous material from agricultural wastes. Animal manure is anaerobically digested to form a gaseous product containing methane and a sludge containing nitrogen and consisting of liquid and solid phases. A cellulosic crop residue is mildly pretreated in particulated form with an aqueous sodium hydroxide solution to form a slurry of the pretreated crop material and spent sodium hydroxide solution. The sludge and slurry then are combined to form a fermentation medium containing sufficient nutrient elements to effect fungal fermentation. The fermentation medium is sterilized and inoculated with a culture of the fungus, *Chaetomium cellulolyticum*. The fungus is aerobically fermented in the fermentation medium to provide a fermented solid mass consisting of about 20 to about 80% DM of the fungus and the balance of unfermented crop residue. The solid mass is separated from the fermentation medium. After separation from the fermentation medium, the solid mass usually is dried to a moisture level below about 10% by weight.

In the process of the invention, therefore, pretreated manure and pretreated crop residue are combined to provide all the nutrients required for fungal growth, so that no additions of nutrients from external sources are required. While pretreatments of the manure and crop residues are effected, all the materials resulting from the pretreatments, including solid and liquid phases, are carried forward to the fermentation medium and hence are not harmful by-products of the process.

GENERAL DESCRIPTION OF THE INVENTION

The animal manure which is used in the fermentation medium in this invention usually consists of both feces and urine and is first anaerobically digested under any convenient conditions to render the nutrients more available to the microorganism.

Such anaerobic digestion may be effected under mesophilic or thermophilic conditions, as desired. Mesophilic anaerobic fermentation usually is effected at a temperature of about 35° C. to about 40° C. for an average residence time of about 10 to about 14 days. Thermophilic anaerobic fermentation usually is effected at a temperature of about 50° to about 60° C. for an average residence time of about 8 to about 10 days.

The anaerobic digestion of the animal manure, such as, cattle or swine manure, produces a sludge containing dissolved nitrogenous nutrients and volatile fatty acids. The whole of the anaerobic sludge, including liquid and solid phases, are used directly in the formation of the fermentation medium for aerobic fermentation. A by-product gas containing methane is also formed in the anaerobic digestion step and may be used as a heating fuel.

The pretreatment of the cellulosic crop residue, such as a cereal grain straw, involves contact with dilute alkali to soften the cellulosic material and render the same susceptible to fermentation by the fungus. The strength of alkali used and the extent of pretreatment effected depends on the proportion of microbial biomass, and hence protein content, of the product which is desired. A minimum pretreatment corresponds to a product containing at least about 20% DM of microbial biomass while the maximum pretreatment corresponds to a product containing 100% DM of biomass. Preferably, the pretreatment is effected to achieve a biomass content of about 20 to about 80% DM, or about 9 to about 36% DM of protein.

In a first pretreatment procedure, hot alkali in the form of sodium hydroxide solution is used to achieve the softening. The sodium hydroxide is utilized in this procedure in a concentration in the range from about 0.25 to about 1.0% W/W NaOH and the pretreatment is effected at any convenient temperature in the range from about 60° to about 121° C. The reaction time required to effect the pretreatment varies interdependently with the temperature and is in the range of from about 120 to about 15 minutes. A typical set of conditions is 121° C. for 20 minutes using 0.5% NaOH.

A second pretreatment procedure involves a combination of the use of cold alkali in the form of sodium hydroxide solution and gamma radiation. The sodium hydroxide solution is utilized in this second procedure in a concentration in the range from about 3 to about 6% W/W NaOH and at an ambient room temperature of about 15° to about 30° C. The gamma radiation is applied at a dosage level of about 10 to about 50 megarads. The time required for pretreatment varies interdependently with the radiation dosage and is in the range of from about 120 to about 60 minutes. A typical set of conditions is 10 megarads for 120 minutes using 4% NaOH at 25° C. The source of gamma radiation may be any convenient gamma-ray-emitting material, and is conveniently a gamma-ray-emitting nuclear waste material.

The cellulosic crop residue is particulated prior to commencement of the pretreatment and the pretreatment usually is effected at a solids concentration of about 5 to about 30% W/W. If used in granular form, the particles may have an average particle size in the range of about 1 to about 5 mm. If used in fibrous forms, fibre sizes up to 2 cm in length may be used.

The slurry of pretreated cereal grain straw or other crop residue and pretreatment medium which results from the pretreatment step is used in the formation of the sterile fermentation medium. In prior procedures where proteinaceous material has been formed from pretreated cellulosic material, the pretreatment medium has been discarded, presenting a potential pollution hazard and a waste of valuable nutrient materials, as explained in more detail below.

It will be known that a microorganism utilizes certain essential elements for its growth in specific proportions which vary to a minor degree from organism to organism, but generally the major elements of carbon, nitrogen, phosphorus and potassium are utilized in the ratio of C:N:P:K of 100:10:1:1 by weight, and hence this ratio typically is provided in a fermentation medium. The proportions of these elements may vary, however, but the organism will leave unutilized any excess proportion of any given element.

In the present invention, the material resulting from pretreatment of the manure and pretreatment of the crop residue are combined in proportions suitable to form a fermentation medium containing the relative proportions of nutrients suitable for fermentation of the fungus.

The pretreated crop residue provides the main carbon source while the pretreatment medium resulting from the crop residue pretreatment effectively provides all the non-carbon nutrient elements required other than nitrogen, as a result of the solubilization of elements such as phosphorus and potassium from the crop residue during the pretreatment. The pretreated manure provides the nitrogen source for the fermentation medium. Following mixing of the products of the pretreatment steps to form the fermentation medium, the fermentation medium is sterilized.

The consistency of the sterile slurry mixture of fermentation medium usually is that suitable for conventional submerged fermentation techniques, such as, up to about 3% W/V solids. The fermentation, however, may be effected at any desired concentration allowable by conventional solid state fermentation techniques, at an overal solids concentration of generally up to about 30% W/W.

The fermentation medium is adjusted, if necessary, to a pH in the range of about 5 to about 7 and inoculated with the fungus, *Chaetomium cellulolyticum*. Aerobic fermentation is effected at a temperature of about 30° to about 40° C., typically around 37° C., using sterile air, typically at a flow rate of 1 to 2 volumes of air per unit volume of medium per minute.

During the fermentation, the fungus uses the cereal grain straw or other cellulosic crop residue to reproduce itself and to generate cellulase-enzymes, which soften and thereby improve the digestibility of any solid cereal grain straw which remains unutilized. The fermentation is continued until the desired fungus growth has been effected, for example, for about 12 to about 24 hours, if conducted batchwise. In continuous operations, an average residence time of the mixture in the fermentor is typically 4 to 8 hours for adequate growth.

The rate of fermentation may be accelerated by from about 25 to 30% by the incorporation in the fermentation medium of small amounts, usually about 0.01 to about 0.03% W/V, of a carboxypolymethylene.

Following completion of the fermentation, the solid phase usually is separated from the aqueous phase. The separated solid phase may be used as such, or may be dried to a low moisture content, generally below about 10% W/W, typically about 8% W/W. The liquid phase may be reused, if desired.

The solid phase product contains *Chaetomium cellulolyticum* in variable quantities, depending on the extent and pretreatment and the fermentation. The product contains from about 20 to about 80% DM, and up to 100% DM. The remainder of the solid phase is unfermented crop residue. Products having a biomass content greater than about 55% DM may be used as ruminant and non-ruminant feed while products having a biomass content less than this value may be used primarily as ruminant feed.

The proteinaceous products resulting from the process of the invention have been found by in-vivo and in-vitro feeding trials to be suitable as an animal feed supplement for non-ruminant and ruminant animals and poultry.

*Chaetomium cellulolyticum* is a fungus freely available from the American Type Culture Collection (ATCC No. 32319) and has the following capabilities: (1) utilization of a variety of cellulosic as well as non-cellulosic carbohydrate materials as carbon nutrient for growth, (2) utilization of a variety of synthetic as well as non-synthetic mixtures as non-carbon nutrient supplement for growth, (3) growth over a range of pH of about 5 to 8, the optimal being about pH 5 for insoluble cellulose and about pH 7 for solubilized hemicellulose and, (4) growth over a range of temperatures of about 30° C. to 45° C., the optimal being about 37° C.

The average composition of the fungus is as follows (%DM basis): 45% crude protein, 40% carbohydrates, 10% fats, 5% vitamins, minerals, etc. The following Table shows that the amino acid profile of the protein component of the fungus is nutritionally sound and is comparable with fodder yeast (*C. utilis*), soymeal protein and the UN-FAO reference protein for human nutrition.

TABLE

| Amino Acid | C. cellulolyt-icum | C. utilis | Soy-meal | FAO reference |
|---|---|---|---|---|
| Threonine | 6.1 | 5.5 | 4.0 | 2.8 |
| Valine | 5.8 | 6.3 | 5.0 | 4.2 |
| Cystine | 0.3 | 0.7 | 1.4 | 2.0 |
| Methionine | 2.3 | 1.2 | 1.4 | 2.2 |
| Isoleucine | 4.7 | 5.3 | 5.4 | 4.2 |
| Leucine | 7.5 | 7.0 | 7.7 | 4.8 |
| Tyrosine | 3.3 | 3.3 | 2.7 | 2.8 |
| Phenylalamine | 3.8 | 4.3 | 5.1 | 2.8 |
| Lysine | 6.8 | 6.7 | 6.5 | 4.2 |

The procedure of the invention, therefore, enables agricultural waste materials, including manures and cellulosic crop residues, to be converted economically to proteinaceous product for animal consumption in a unique procedure which is fundamentally different from prior procedures for treatment of agricultural waste material.

BRIEF DESCRIPTION OF DRAWING

The sole FIGURE of the accompanying drawing is a schematic flow sheet of one preferred embodiment of the invention for the formation of proteinaceous animal feed from agricultural wastes.

DESCRIPTION OF PREFERRED EMBODIMENT

The waste treatment system 10 consists essentially of several interconnected subsystems, namely, an anaerobic digester 12 utilizing animal manure fed by line 14; a thermochemical hydrolyzer 18 wherein cellulosic crop wastes and residues fed by line 20 are treated with alkaline chemicals fed by line 22 to soften the cellulosic material; and an aerobic fermentor 24 wherein a microorganism is cultivated on a mixture of the product formed in the pretreatment unit 18, and the product from the anaerobic digester 12, these materials being forwarded respectively by lines 26 and 28 to a preparation unit 30 wherein temperature and pH adjustments are made and the fermentation medium sterilized prior to forwarding to the fermentor 24.

When the desired degree of microorganism growth has occurred in the fermentor 24, the mixture of biomass-containing solid phase and liquid phase are forwarded by line 32 to a separator 34, for separation of the solid and liquid phases, the liquid phase being recycled, if desired, by line 36 to the anaerobic digester 12 and/or the pretreatment unit 18.

The solid mass containing proteinaceous biomass may be used as such, or forwarded by line 38 to a drier 40 wherein the solid phase is dried to a desired moisture content, generally 6 to 10% by weight, to provide a proteinaceous product in line 42 suitable for storage or direct use as an animal feed supplement.

The anaerobic digestion of the manure in the fermentor 24 produces by-product methane in line 44, which may be stored and used as a heating fuel, such as for the pretreatment unit 18 or the drier 40.

The conditions of operation of the anaerobic digester 12, the thermochemical pretreatment 18 and the aerobic fermentor have been discussed in detail above in the detailed discussion of the individual process steps of the invention. Such conditions need not, therefore, be repeated here.

The system described above with reference to the drawing may be run continuously or in a cyclic batch mode with any convenient cycle time, such as, 24 hours. In such a cyclic batch mode, the anaerobic digestion unit 12 is fed intermittently and at the same time an equivalent volume of digester sludge is withdrawn by line 28 and used to prepare the medium for the aerobic fermentation. Similarly, at the end of the fermentation period in the fermentor 24, about 90% of the fermentor contents may be removed for further processing while the remaining 10% is used as inoculum for the next batch.

In view of its modular design, the waste treatment system 10 may be converted into alternative configurations, in the event of an equipment breakdown or a different feed ration is desired. These options permit the utilization of undigested manure as the supplementary nutrient source, in the event of malfunction of the anaerobic digester.

EXAMPLES

Example 1

Cattle manure (feces and urine) at 7.5% DM (dry matter by weight) concentration was fed to an anaerobic digester. The digester conditions were: inlet pH 6.4, temperature 39° C., digester pH 7.1, and average retention time 14 days.

During a 14-day run, the digester was fed daily with the cow manure slurry and an appropriate volume removed to retain a substantially constant volume in the digester. At the end of the two-week period, the digester performance stabilized yielding an average gas composition of 60% methane, 30% carbon dioxide, with the balance being mainly hydrogen and nitrogen compounds, and an average of 7.6 g/l TKN (total Kjeldahl nitrogen) and an average of 1.3 g/l volatile fatty acids (measured as acetic acid) in the anaerobic liquor.

Chopped cornstover and 1% W/V NaOH solution were fed to a reactor at a solids-to-liquid ratio of 1 to 10 by weight and the reactor contents were heated to 121° C. using steam and maintained at that temperature for 20 minutes. The resultant slurry mixture consisted of a solubilized hemicellulose solution and swollen partially delignified cellulose material, which is fermentable with certain fungi.

The product resulting from the anaerobic digestion of the manure and the slurry resulting from the alkaline treatment of cornstover were combined to form a fermentation medium having C:N ratio of 8:1. The fermentation medium was sterilized, adjusted to a pH of 6.5 and inoculated with a culture of *Chaetomium cellulolyticum*.

The *Chaetomium cellulolyticum* was aerobically fermented using standard submerged fermentation techniques at 37° C. and at an air flow rate of 2 v/v/m. After a fermentation period of 14 hours, the solid product contained fungi in an amount of 49% DM.

Example 2

The procedure of Example 1 was repeated using anaerobically predigested swine manure (feces and urine) and wheat straw. In the anaerobic predigestion, the following parameters were employed: inlet pH 6.5, temperature 39° C., digester pH 7, average retention time 8 days. After a 14-day period, the digester stabilized yielding a 60% methane effluent gas and 2.8 g/l of nutrient nitrogen in the anaerobic liquor.

After a fermentation period of 21 hours in the fermentation medium, the solid product contained 56% DM of the fungus.

In summary of this disclosure, the present invention provides waste utilization processes conducted on agricultural waste materials producing beneficial end products. Modifications are possible within the scope of this invention.

What I claim is:

1. A process for the formation of proteinaceous material from agricultural waste, which consists of:
   (a) anaerobically digesting animal manure to form a gaseous product containing methane and a sludge containing nitrogen and consisting of liquid and solid phases, said anaerobic digestion being effected under mesophilic or thermophilic anaerobic fermentation conditions,
   (b) pretreating a crop residue in particulated form with a dilute aqueous solution of sodium hydroxide to form a slurry of the pretreated crop residue in solid form and spent sodium hydroxide solution, said pretreatment being effected either:
   (i) using an aqueous sodium hydroxide solution at a concentration of about 0.25 to about 1.0% W/W NaOH at a temperature of about 60° to 121° C. for a time of about 120 to about 15 minutes, or (ii) using an aqueous sodium hydroxide solution at a concentration of about 3 to about 6% W/W NaOH at a temperature of about 15° to about 30° C. while being subjected to gamma radiation at a dosage level of about 10 to about 50 megarads for a time of about 120 to about 60 minutes;

(c) mixing the sludge formed in step (a) with the slurry formed in step (b) without separating any component therefrom to form a fermentation medium having a solids concentration of up to about 30% W/W and containing sufficient nutrient elements to effect fungal fermentation;

(d) sterilizing said fermentation medium and adjusting the pH of the resulting sterile fermentation medium to a value within the range of about 5 to about 7 if not already at a pH value within said range;

(e) inoculating said sterile fermentation medium with a culture of the fungus *Chaetomium cellulolyticum;*

(f) aerobically fermenting said fungus in the sterile inoculated fermentation medium formed in step (e) at a temperature of about 30° to about 40° C. for a time sufficient to provide a fermented solid mass consisting of about 20 to about 100% DM of the fungus and any balance of unfermented crop residue; and (g) separating said solid mass formed in step (f) from the fermentation medium.

2. The process of claim 1 wherein said anaerobic fermentation is effected under mesophilic fermentation conditions of about 30° to about 40° C. for about 10 to about 14 days.

3. The process of claim 1 wherein said anaerobic fermentation is effected under thermophilic fermentation conditions of about 50° to about 60° C. for about 8 to about 10 days.

4. The process of claim 1 wherein said fermentation step (f) is effected to provide a fermented solid mass consisting of about 20 to about 80% DM of the fungus and the balance of unfermented crop residue.

5. The process of claim 4 including the additional step of drying the solid phase separated in step (g) below about 10% W/W.

6. The process of claim 4 wherein the residual fermentation medium remaining after separation of the solid phase in step (g) is recycled to the anaerobic digester step (a) and/or to the pretreatment step (b).

7. The process of claim 1 wherein the crop residue is selected from the group consisting of cereal grain straws and bagasse.

8. The process of claim 7 wherein the cereal grain straw is cornstover.

9. The process of claim 7 wherein the cereal grain straw is wheat straw.

10. The process of claim 1 wherein the fermentation medium used in step (f) additionally contains about 0.01 to about 0.3% W/V of a carboxy polymethylene.

11. The process of claim 1 wherein said pretreatment step (b) is effected at a temperature of about 120° C. for about 20 minutes using 0.5% W/V NaOH solution.

12. The process of claim 1 wherein said pretreatment step (b) is effected at a temperature of about 25° C. for about 120 minutes or an applied gamma radiation of 10 megarads using about 4% W/W NaOH solution.

* * * * *